(12) United States Patent
Nelson et al.

(10) Patent No.: US 6,479,822 B1
(45) Date of Patent: Nov. 12, 2002

(54) SYSTEM AND METHOD FOR TERAHERTZ FREQUENCY MEASUREMENTS

(75) Inventors: Keith A. Nelson, Newton, MA (US); Timothy Crimmins, Portland, OR (US)

(73) Assignee: Massachusetts Institute of Technology, Cambridge, MA (US)

( * ) Notice: Subject to any disclaimer, the term of this patent is extended or adjusted under 35 U.S.C. 154(b) by 13 days.

(21) Appl. No.: 09/611,834

(22) Filed: Jul. 7, 2000

(51) Int. Cl.⁷ .............................. G01N 21/63
(52) U.S. Cl. .............. 250/341.1; 250/338.1; 250/358.1
(58) Field of Search ............. 250/330, 358.1, 250/338.1, 341.1; 359/239; 356/432, 445, 451, 484, 521

(56) References Cited

U.S. PATENT DOCUMENTS

| | | |
|---|---|---|
| 5,682,262 A | 10/1997 | Wefers et al. |
| 5,710,430 A | 1/1998 | Nuss |
| 5,719,650 A | 2/1998 | Wefers et al. |
| 5,734,470 A | 3/1998 | Rogers et al. |
| 5,748,317 A * | 5/1998 | Maris et al. ............... 356/357 |
| 5,789,750 A | 8/1998 | Nuss |
| 5,894,125 A | 4/1999 | Brener et al. |
| 5,991,048 A * | 11/1999 | Karlson et al. ............. 356/445 |
| 5,999,308 A | 12/1999 | Nelson et al. |
| 6,075,640 A | 6/2000 | Nelson |

OTHER PUBLICATIONS

D.M. Mittleman et al., *IEEE Journal of Selected Topics in Quantum Electronics, T–Ray Imaging*, 2:679–692 (1996).
M.C. Nuss, *IEEE, Chemistry Is Right for T–Ray Imaging*, (Mar. 1996).
P.R. Smith et al., *IEEE Journal of Quantum Electronics, Subpicosecond Photoconducting Dipole Antennas*, 24:255–260 (1988).
F. Vallee et al., *Physical Review Letters, Picosecond Phonon–Polariton Pulse Transmission Through An Interface*, 74:3281–3284 (1995).

* cited by examiner

*Primary Examiner*—Constantine Hannaher
*Assistant Examiner*—Timothy J Moran
(74) *Attorney, Agent, or Firm*—Fish & Richardson P.C.

(57) ABSTRACT

A spectroscopic method for characterizing a sample including: positioning the sample adjacent to a non-centrosymmetric material; directing at least one temporal pulse of coherent EM radiation into the non-centrosymmetric material to generate a polariton therein and cause EM radiation from the polariton to propagate into the sample, wherein the polariton has a frequency less than or equal to the bandwidth of the pulse; and measuring a response of the sample to the EM radiation from the polariton.

37 Claims, 7 Drawing Sheets

SYSTEM AND METHOD FOR TERAHERTZ FREQUENCY MEASUREMENTS

This invention was made with government support under Grant Number CHE-9713388 awarded by the National Science Foundation. The government has certain rights in the invention.

BACKGROUND OF THE INVENTION

The invention relates to systems and methods for making spectroscopy and metrology measurements using electromagnetic radiation, particularly, electromagnetic radiation in the terahertz frequency range.

Measurements with electromagnetic radiation are now conducted in essentially every range of the electromagnetic spectrum, ranging at least from x-rays through radio waves. Different regions of the spectrum are well suited for measurements of different materials and different material properties.

Not all regions of the electromagnetic spectrum are equally accessible for measurements. In some cases, generation of the electromagnetic radiation with the desired frequencies/wavelengths, tunability, intensity, pulse duration or other waveform characteristics may be difficult or costly. In other cases detection of the radiation with the desired sensitivity, time or frequency resolution, or other features may pose challenges. Finally the convenient use of the radiation for practical measurements may present additional difficulties, depending on the geometry of radiation generation and detection and of sample placement and on other factors.

The terahertz frequency range (e.g., 0.1–20 THz) or correspondingly the far-infrared ("far IR") wavelength range, is emerging as an important component in the spectroscopic study and optical imaging of a very wide range of samples extending from simple and complex liquids to biological materials to integrated circuits. For example, in liquids and partially ordered solids, the terahertz frequency regime probes properties on length and time scales intermediate between those characteristic of bulk low-frequency dielectric responses and of local intermolecular or interionic motions. Conventional dielectric spectroscopy rarely reaches frequencies over 100 GHz, and therefore components of the dynamics of complex materials such as supercooled liquids and mixed ferroelectric crystals remain elusive.

Unfortunately, there can be experimental challenges to generating and detecting terahertz radiation. Microwaves, which border terahertz-rays on the low frequency side, are typically generated using high frequency electronics while infrared waves, on the high frequency border, are generated by light sources, usually via blackbody radiation or lasers. Recently, femtosecond lasers producing optical pulses on the order of 100 fs or less have been used to illuminate photoconducting dipole antennas, which respond by generating broad bandwidth, coherent bursts of far-IR output with substantial spectral density from 100 GHz to 5 THz or higher. Such terahertz radiation, which propagates through free space, is focussed and/or collimated with far-IR optics, and can be detected using another, similar photoconductive dipole antenna, which is gated by a variably delayed femtosecond pulse.

SUMMARY OF THE INVENTION

The invention features a system and method for generating terahertz radiation by time-domain excitation of polaritons in a nonlinear optical crystal. One or more pulses of coherent optical radiation illuminate a non-centrosymmetric material to excite a polariton having a frequency less than or equal to the bandwidth of the excitation pulses. Spatial and temporal shaping of the optical excitation pulses can control the frequency, bandwidth, and propagation properties of the polariton. When the polariton propagates to the edge of the non-centrosymmetric material, its electromagnetic component can couple into an adjacent sample as terahertz radiation. The interaction between the sample and the terahertz radiation can be measured a number of ways.

For example, after its interaction with the sample, the terahertz radiation can couple into a second non-centrosymmetric material as a polariton, whose properties can be detected by a second set of one or more optical pulses. Alternatively, for example, the terahertz radiation can reflect back to the original non-centrosymmetric material for the optical detection measurement. In either case, the attenuation and delay of the detected terahertz radiation reveals the real and imaginary components of the dielectric properties of the sample in the terahertz regime. Moreover, the sample can be probed directly with, e.g., an optical beam, following its interaction with the terahertz radiation. Measurements can be repeated at additional polariton frequencies in an automated fashion to spectrally resolve the dielectric response of the sample.

In general, in one aspect, the invention features a spectroscopic method for characterizing a sample. The method includes: positioning the sample adjacent to a non-centrosymmetric material; directing at least one temporal pulse of coherent EM radiation into the non-centrosymmetric material to generate a polariton therein and cause EM radiation from the polariton to propagate into the sample, wherein the polariton has a frequency less than or equal to the bandwidth of the pulse; and measuring a response of the sample to the EM radiation from the polariton.

Embodiments of the method can include any of the following features.

The measuring step can include: positioning a second non-centrosymmetric material to receive EM radiation from the sample in response to the EM radiation from the polariton in the first-mentioned non-centrosymmetric material, wherein the EM radiation from the sample propagates into the second non-centrosymmetric material to form another polariton; and directing additional EM radiation to interact with the polariton in the second non-centrosymmetlic material; and measuring a response of the second non-centrosymmetric material to the interaction of the additional EM radiation and the polariton in the second non-centrosymmetric material. Furthermore, the response of the second non-centrosymmetric material can be measured by measuring at least one of transmission, reflection, polarization rotation, and diffraction of the additional EM radiation by the polariton in the second non-centrosymmetric material. Moreover, the at least one of the transmission, reflection, polarization rotation, and diffraction of the additional EM radiation can be spectrally resolved. The response of the second non-centrosymmetric material can also be one of sum-frequency generation and difference-frequency generation caused by the interaction of the additional EM radiation and the polariton in the second non-centrosymmetric material. Furthermore, the response of the second non-centrosymmetric material can also be measured by using the additional EM radiation to image the polariton in the second non-centrosymmetric material. The measured response of the second non-centrosymmetric material can be indicative of the amplitude and phase of the polariton in the second non-centrosymmetric material.

The measuring step can also include: directing additional EM radiation to interact with the EM radiation in the sample from the polariton; and measuring a response of the sample to the interaction of the additional EM radiation and the EM radiation in the sample from the polariton. The measuring step can include measuring at least one of diffraction, reflection, a change in absorption, and a change in polarization of the additional EM radiation by the sample caused by the presence of the EM radiation in the sample from the polariton. Moreover, the measured at least one of diffraction, reflection, the change in absorption, and the change in polarization can be spectrally resolved. Also, the response can be one of sum-frequency generation and difference-frequency generation caused by the interaction of the additional EM radiation and the EM radiation in the sample from the polariton.

The EM radiation from the polariton can also reflect from a reflecting surface and back into the non-centrosymmetric material to form a second polariton, in which case, the measuring step can include: directing additional EM radiation to interact with the second polariton; and measuring a response of the non-centrosymmetric material to the interaction of the additional EM radiation and the second polariton.

The measured response can be indicative of absorption by the sample, refractive index of the sample, and/or complex refractive index of the sample, at the frequency of the EM radiation from the polariton.

The method can further include repeating the positioning, directing, and measuring for a reference sample, and comparing the measurements of the first-mentioned sample and the reference sample. The method can further include temporally shaping EM radiation to form the at least one temporal pulse. The directing step can include directing a spatially periodic pattern of the at least one temporal pulse of EM radiation onto the non-centrosymmetric material. The method can further include selecting the period of the spatially periodic pattern to produce a selected frequency for the polariton. The directing step can further include crossing at least two beams of the at least one temporal pulse of EM radiation to form the spatially periodic pattern. Alternatively, the directing step can further include passing EM radiation through a mask to produce the spatially periodic pattern on the non-centrosymmetric material. The method can further include repeating the selecting, directing, and measuring steps for multiple frequencies of the polariton. The method can further include focusing the EM radiation from the polariton prior to it reaching the sample.

The sample can be one of a liquid, solid, and gas. It can separated from the non-centrosymmetric material. The frequency of the polariton can be the range of about 0.1 to 20 THz, e.g., in the range of about 1 to 10 THz.

In general, in another aspect, the invention features an apparatus for characterizing a sample including: a non-centrosymmetric material; a sample assembly configured to support the sample adjacent to the non-centrosymmetric material; a light source which during operation directs at least one temporal pulse of coherent EM radiation into the non-centrosymmetric material, the at least one temporal pulse having an intensity and bandwidth sufficient to generate a polariton in the non-centrosymmetric material and cause EM radiation from the polariton to propagate into the sample, wherein the polariton has a frequency less than or equal to the bandwidth of the pulse.

Embodiments of the apparatus can include any of the following features.

The apparatus can further include: a second non-centrosymmetric material positioned to receive EM radiation from the sample in response to the EM radiation from the polariton in the first-mentioned non-centrosymmetric material, wherein during operation the EM radiation from the sample propagates into the second non-centrosymmetric material to form another polariton, wherein during operation the light source directs a probe beam of EM radiation to interact with the polariton in the second non-centrosymmetric material; and a detector positioned to measure a response of the second non-centrosymmetric material to the interaction of the probe beam and the polariton in the second non-centrosymmetric material. The apparatus can further include a computer coupled to the light source and the detector, wherein during operation the computer analyzes the measured response to characterize the sample.

During operation of the apparatus, the light source can direct a probe beam of additional EM radiation to interact with the EM radiation in the sample from the polariton, and the apparatus can further include a detector positioned to measure a response of the second non-centrosymmetric material to the interaction of the probe beam and the polariton in the second non-centrosymmetric material. The apparatus can further include a computer coupled to the light source and the detector, wherein during operation the computer analyzes the measured response to characterize the sample.

The sample assembly can includes a reflecting surface configured to reflect the EM radiation from the polariton back into the non-centrosymmetric material to form a second polariton. During operation the light source can direct a probe beam of additional EM radiation to interact with the second polariton, and the apparatus can further include a detector positioned to measure a response of the non-centrosymmetric material to the interaction of the additional EM radiation and the second polariton.

During operation the light source can cause the at least one temporal pulse to form a periodic spatial pattern in the non-centrosymmetric material. The apparatus can further include a computer coupled to the light source to control the period of the periodic spatial pattern. To form the periodic spatial pattern, the light source can direct a pair of excitation beams to interfere in the non-centrosymmetric material, the pair of excitation beams including the at least one temporal pulse. Alternatively, the light source can include a laser source, a phase mask, and one or more imaging lenses, wherein during operation the laser source directs a beam to the phase mask, the phase mask diffracts the beam into multiple orders, and the one or more imaging lenses recombines the multiple orders in the non-centrosymmetric material to form the periodic spatial pattern.

Embodiments of the invention have many advantages.

For example, systems and methods described herein can be used to generate and/or detect terahertz frequency radiation without the use of a photoconductive dipole antenna. Such systems may be used as terahertz frequency spectrometers that involve only optical beams. Moreover, spatial shaping of the optical excitation pulses used to generate the polaritons can control the frequency of the polariton and the electromagnetic radiation derived there from. Thus, the systems can be automated to scan the sample with multiple, narrow-band pulses of terahertz radiation.

Other features and advantages of the invention will be apparent from the following detailed description, and from the claims.

DETAILED DESCRIPTION

The invention features methods and systems for generating terahertz radiation for use in spectroscopic and other measurements by way of time-domain optical excitation of polaritons in non-centrosymmetric materials. Visible light is used to generate terahertz frequency radiation in a geometry that is convenient for irradiation of a sample, and visible light is used to detect the terahertz frequency radiation after its interaction with the sample, thereby permitting convenient sample characterization in the terahertz frequency range.

Figure 1:
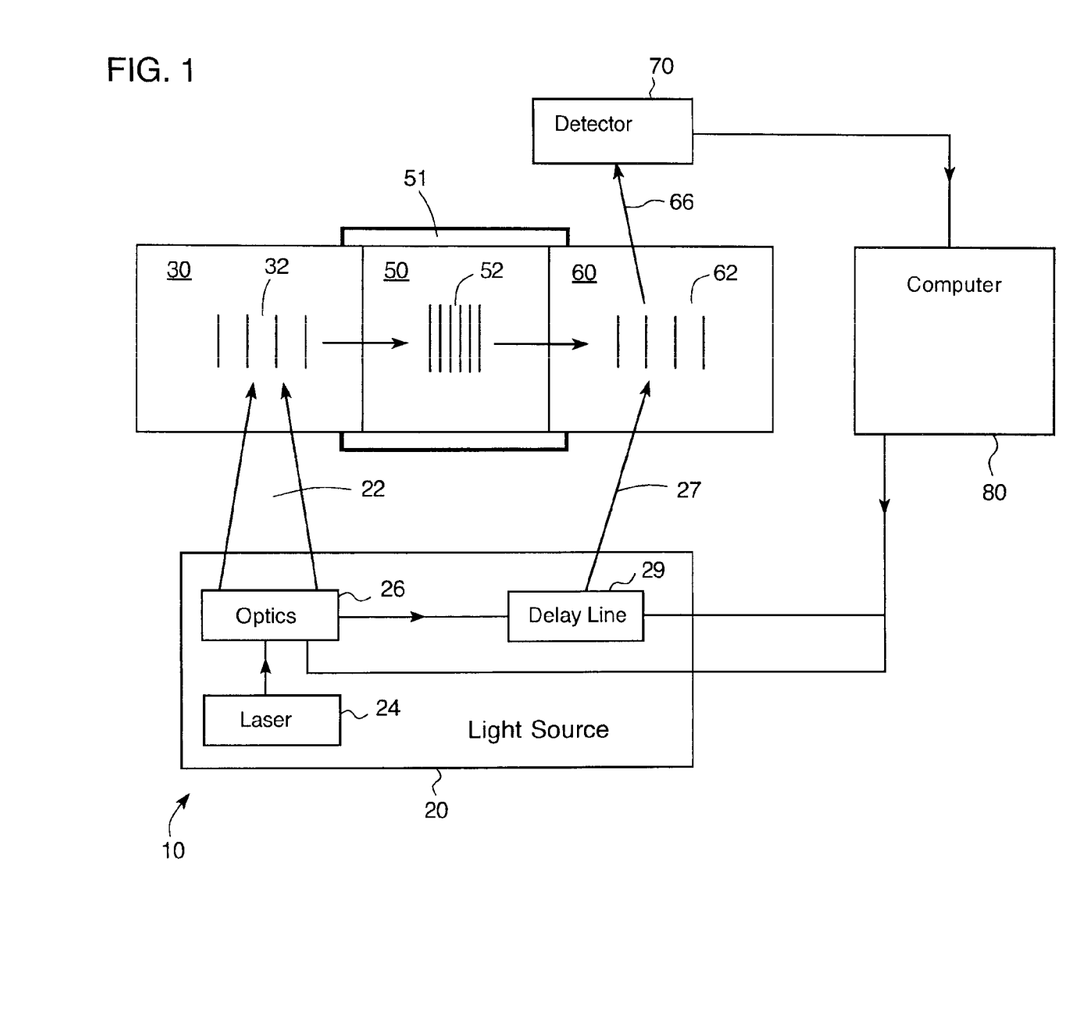
FIG. 1 is a schematic drawing of terahertz frequency spectrometer.

Referring to FIG. 1, a schematic diagram of a terahertz frequency spectrometer 10 is shown. An optical light source 20 directs a pair of excitation beams 22 to spatially overlap and interfere with one another to form a grating pattern in a first non-centrosymmetric crystal 30. The coherent bandwidth of the excitation beams 22 is sufficient to excite a polariton 32 in crystal 30 corresponding to the wavevector of the grating pattern. Polariton 32 propagates to the edge of crystal 30 where its electromagnetic component then couples into sample 50 as electromagnetic terahertz radiation 52. The dielectric and other properties of sample 50 can attenuate, retard, and/or otherwise alter the properties of terahertz radiation 52, which, following its interaction with sample 50, couples into a second non-centrosymmetric crystal 60 as another polariton 62. A sample assembly 51 is configured to support the sample adjacent non-centrosymmetric crystal 30. The lines depicting polaritons 32 and 62, and terahertz radiation 52 in FIG. 1 indicate the amplitude peaks of the respective waves at particular times. Light source 20 directs a temporally delayed probe beam 27 to interact with polariton 62 and produce a signal beam 66, whose intensity is measured by a detector 70. A computer 80 is coupled to the detector 70 and light source 20 to analyze the signal measured by detector with the respect to the properties of the excitation beams 22 and the probe beam 27. The properties can include the wavevector of the grating pattern produced by the excitation beams and the temporal delay between the probe and excitation beams.

First non-centrosymmetric crystal 30 functions as an "excitation" crystal, generating polariton 32 following optical excitation. Second non-centrosymmetric crystal 60 functions as a "detection" crystal in which polariton 62 manipulates (e.g., diffracts) probe beam 27 to produce signal beam 66. Sample 50 is positioned between the excitation and detection crystals to couple terahertz radiation from the excitation crystal, and to the detection crystal. Accordingly, in this embodiment, terahertz frequency spectrometer 10 requires only optical input and output beams.

A polariton is a wave that couples an electromagnetic field component with a material component in a polar or polarizable medium. For example, phonon-polaritons are waves that couple an electromagnetic (EM) field with a molecular or lattice displacement. The frequencies for such phonon-polaritons are in the range of about 0.1 THz to 20 THz, and typically in the range of about 1 to 10 THz, which correspond to ranges of interest for the generation of electromagnetic terahertz radiation. For a general reference on polaritons, see, e.g., Charles Kittel in *Introduction to Solid State Physics* (John Wiley and Sons, 1996).

One mechanism for generating a polariton is impulsive stimulated Raman scattering (ISRS), which generally occurs in materials that have Raman-active lattice modes (e.g., non-centrosymmetric materials). In ISRS, an ultrashort (e.g., typically less than 200 fs), optical excitation pulse exerts a sudden ("impulse") force on those Raman-active modes whose vibrational periods are longer than the pulse duration. This sudden driving force produces time-dependent vibrational oscillations in the material. For a general reference on ISRS see, for example, Y. Yan and K. A. Nelson (*J. Chem Phys.*, 87:6240, 1987). In non-centrosymmetric materials where one or more of the excited Raman-active vibrational modes are polar, the time-dependent vibrational oscillations correspond to coherent oscillating dipoles, which generate and couple to electromagnetic radiation. Thus, the ISRS excitation excites a coupled response that is part electromagnetic field and part polar lattice vibration, in other words, a phonon-polariton. A related mechanism for generating the polariton is the electro-optic effect, in which the excitation material interacts nonlinearly with the ultrashort optical excitation pulse to rectify the pulse and produce a short burst of terahertz radiation. For a reference on the electro-optic mechanism, see, for example, D. H. Auston and M. C. Nuss (*IEEE J. Quan. Elec.*, 24:184, 1988). However, when the frequency of the rectified optical pulse couples to the polar lattice vibration, the terahertz radiation exists as the electromagnetic component of a phonon-polariton. Thus, both ISRS and the electro-optic effect are mechanisms through which one or more ultrashort optical pulses can produce polaritons in materials with polar, Raman-active modes. Suitable materials include ferroelectric materials such as lithium tantalate ($LiTaO_3$), lead titanate ($PbTiO_3$), potassium niobate ($KnbO_3$), barium titanate ($BaTiO_3$), potassium tantalate niobate ($KTa_{1-x}Nb_xO_3$), PZT ($KZr_xTi_{1-x}O_3$), and PLZT ($K_{1-y}Li_yZr_xTi_{1-x}O_3$). Other non-centrosymmetric materials are also suitable including crystals in the KDP and KTP families and organic crystals such as DAST. Any of the above-mentioned materials can be used for the excitation crystal 30 and the detection crystal 60.

Figure 2:
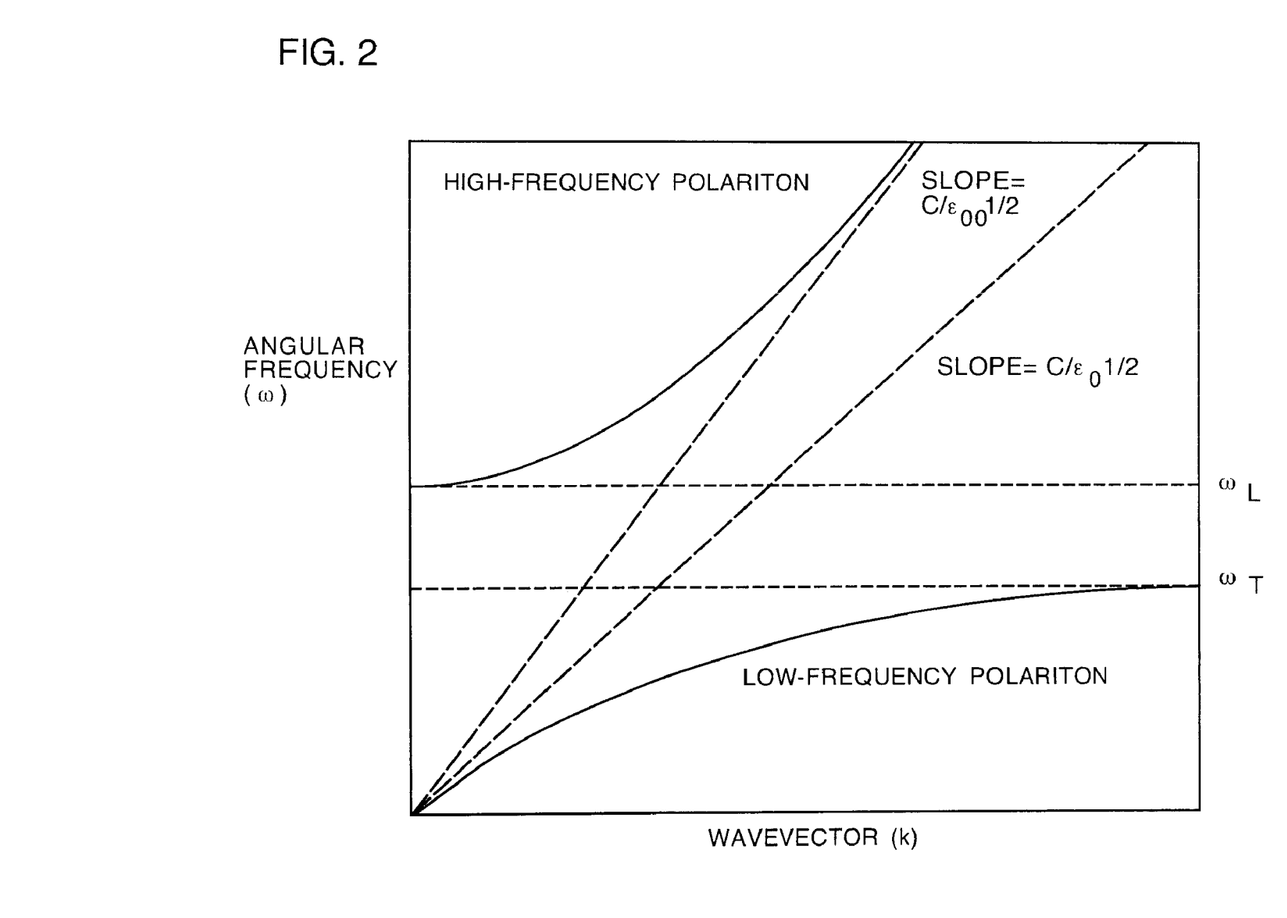
FIG. 2 is an example of a dispersion curve for a phonon-polarition.

Phonon-polaritons occur in a relatively low wavevector regime where the EM frequency is comparable to the frequency of a polar lattice vibration. Because the polar vibration couples to EM radiation, the lattice vibration is dispersive in this wavevector regime and produces propagating responses. FIG. 2 shows a typical dispersion curve for the frequency of a transverse polar lattice vibration in the polariton region in a bulk material. The frequency of the lower branch approaches the transverse optic phonon frequency $\omega_T$ at large wavevector k, while the frequency of the higher branch approaches the longitudinal optic phonon frequency $\omega_L$ at small wavevector k. For a general reference on the excitation of dispersive phonon-polaritons, see, for example, T. P. Dougherty et al. (*J. Opt. Soc. Am. B.*, 9:2179, 1992).

To generate the ultrashort optical pulses used to excite polariton 32 in crystal 30, light source 20 includes a femtosecond laser system 24 producing optical pulses having a duration of, e.g., less than 200 fsec. Suitable laser systems are known in the art and include, e.g., commercially available titanium sapphire laser systems. The excitation of the polariton by ISRS or the electro-optic effect is a non-linear optical process. To produce such a nonlinear interaction the peak intensity of the excitation pulses produced by light source 30 is preferably greater than $1 \times 10^6$ W/cm$^2$, and more preferably greater than $1 \times 10^8$ W/cm$^2$.

Figure 3:
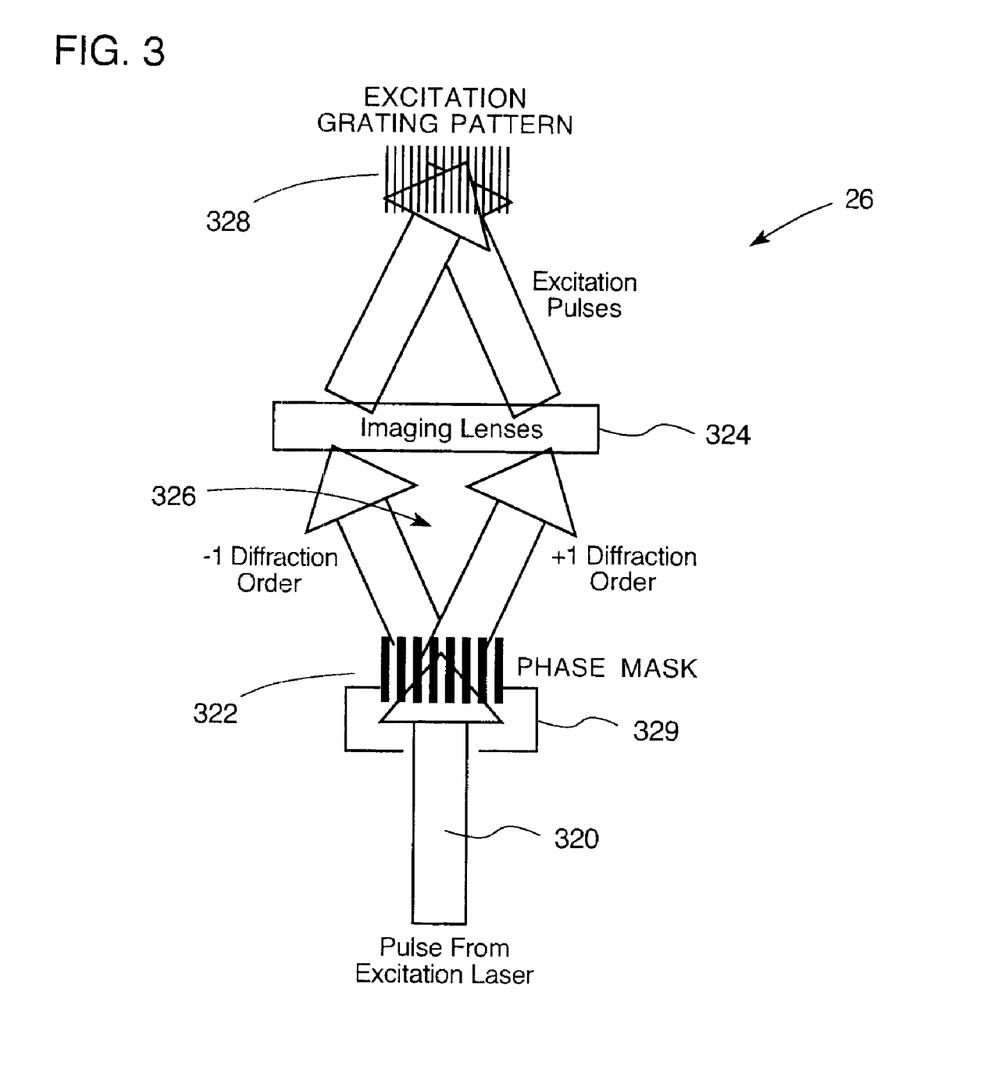
FIG. 3 is a schematic drawing of one embodiment for an optical system in the spectrometer of FIG. 1.

Light source 20 further includes an optical system 26 for converting the output of laser system 24 into the pair of excitation beams 22 that form the grating pattern on crystal 30. As shown in FIG. 3, optical system 26 includes a phase mask 322 and one or more imaging lenses 324 for producing the crossed excitation beams 22. Phase mask 322 includes a diffraction pattern that split the incident beam 320 into different diffractive orders (e.g., +1 and −1) 326. The diffractive orders 326 are incident on the one or more imaging lenses 324, which directs the diffractive orders onto crystal 30 to create the grating pattern 328. The phase mask 322 also includes additional diffraction patterns each having a different periodicity. A positioning stage 329 adjustably positions phase mask 322 relative to incident beam 320 to select the diffraction pattern and the corresponding grating period produced on crystal 30. Positioning stage 329 is coupled to computer 80 to provide automated control over the grating period produced on crystal 30. A cylindrical lens (not shown) can be used to focus the incident beam 320 onto the selected diffraction pattern on phase mask 322. Suitable optical systems employing such a phase mask are described in U.S. Pat. No. 5,734,470 entitled "Device and Method for Time-Resolved Optical Measurements," the contents of which are incorporated herein by reference. Alternatively, optical system 26 can employ conventional beam splitting techniques (e.g., beam splitting optics and mirrors) to adjustably control the angle between two excitation beams focused to overlap on crystal 30 and form a grating pattern.

Referring again to FIG. 1, the period of the grating pattern formed by excitation beams on crystal 30 defines the spatial profile of the impulsive force that excites polariton 32, and correspondingly, defines the central wavevector of polariton 32. In the present case, excitation beams 22 have wavevectors $k_1$ and $k_2$, respectively, and interfere with one another to form the grating pattern, which has a sinusoidal intensity profile having a period equal to $2\pi/q$, where q equals the absolute value of $k_1-k_2$. Within each of the peaks of the sinusoidal intensity profile, the excitation light imparts an impulsive driving force on the Raman active modes within crystal 30. The overall driving force thus corresponds to a driving force having central wavevectors $\pm(k_1-k_2)$. The magnitude of the central wavevectors also specifies the central frequency of polariton 32 according to its dispersion properties in crystal 30 (e.g., based on a dispersion curve such as that shown in FIG. 2). Thus, computer 80 can select the central frequency of polariton 32 by adjusting optical system 26 to select the grating pattern formed on crystal 30.

In other embodiments, optical system 26 can include a mask with a more complex spatial pattern (including amplitude and/or phase modulation), which is mapped onto incident beam 320 and subsequently imaged onto excitation crystal 30. The spatially shaped excitation light drives a polariton response corresponding to the wavevector profile of its intensity. Furthermore, optical system 26 can include optics for temporally shaping incident beam 320, e.g., to produce a series of optical pulses having a repetition rate resonant with polariton to be excited. In general, spatial and temporal shaping of the optical excitation light can be used to tailor the properties of the polariton in crystal 30. See, e.g., U.S. Pat. Nos. 5,682,262 and 5,719,650, the contents of which are incorporated herein by reference, for a description of spatial and/or temporal pulse shaping systems. Furthermore, in other embodiments, a single beam excitation can also generate the polariton. For example, a tightly-focused, ultrashort excitation pulse can generate the polariton based on the difference between wavevectors existing within the tightly-focused pulse (in contrast to the grating pattern). As a result, excitation with a single pulse generates relatively low wavevector polaritons, with the range of wavevectors inversely proportional to the spot size of the excitation pulse.

Referring again to FIG. 1, the grating excitation pattern generates counter-propagating polariton wavepackets with central wavevectors $\pm(k_1-k_2)$, polariton 32 refers to the polariton wavepacket propagating to the edge of crystal 30 adjacent sample 50. Terahertz radiation 52 emerges from the edge of the excitation crystal and propagates into sample 50.

In the presently described embodiment, sample 50 is sandwiched between the excitation and detection crystals, forming an interface with each. In other embodiments, the sample can be separated from one or both of the crystals, with the terahertz radiation propagating in free space. In general, the sample being studied can be a solid, liquid, or gas. Polar liquids and crystals, liquid crystals, biological samples, and glasses may be especially suitable for spectroscopic study in the terahertz frequency regime. The sample being studied can also be spatially homogeneous or heterogeneous, e.g., it can be a patterned or otherwise fabricated material. Where appropriate, sample 50 can include a sample cell assembly to support the sample material. For example, the sample cell assembly can include windows and/or apparatus for loading and removing the sample material.

Many variations of the sample cell geometry could be constructed. For example, a sample cavity such as a trench could be cut into a single non-centrosymmetric crystal, with the crystal regions on opposite sides of the trench defining excitation crystal 30 and detection crystal 60, respectively. Furthermore, a series of trenches or other structures could be constructed so that a periodic array of samples could be examined. For example, spectrometer 10 can include a pair of sample trenches, one for a reference sample and the other for an unknown sample. In additional embodiments, the sample cell size and terahertz frequency can be adjusted to produce a THz-frequency resonator, with potentially increased sensitivity for absorption and other measurements. Also, the crystal edges can be anti-reflection coated to maximize transmission of terahertz radiation through respective interfaces. Moreover, in further embodiments, one or more of the interfaces can be curved to focus the terahertz radiation to a line or point at which the sample is placed, thereby increasing the terahertz radiation intensity at the sample.

Figure 4A:
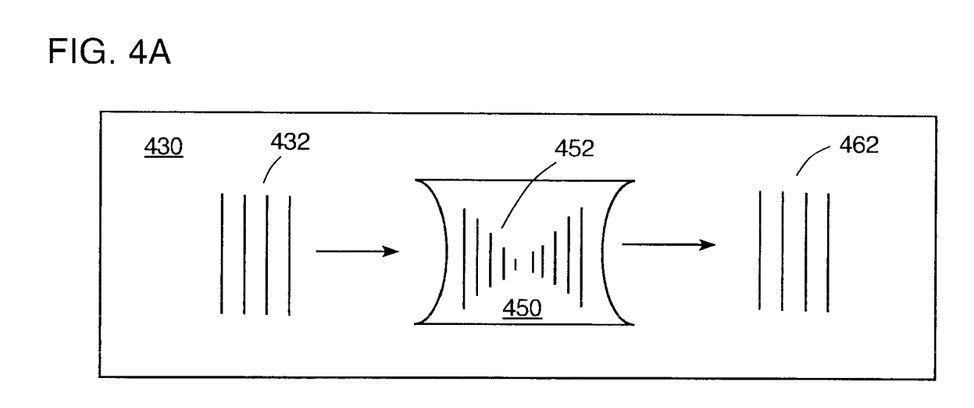
FIGS. 4a and 4b are schematic drawings of different embodiments of a sample cell geometry for the terahertz frequency spectrometer.
Figure 4B:
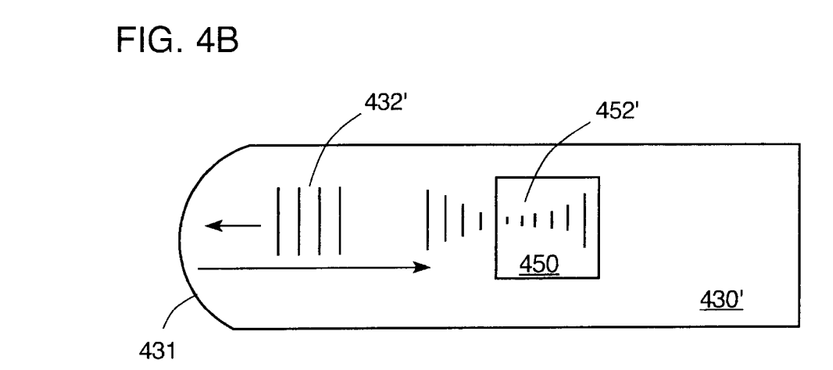

FIGS. 4*a* and 4*b* are schematic diagrams of embodiments for the sample cell geometry. Referring to FIG. 4*a*, a single non-centrosymmetric crystal 430 (e.g., lithium tantalate) forms both the excitation and detection crystals and has a trench drilled into it to form a sample cavity 450. Polariton 432 propagates towards sample cavity 450 and couples terahertz radiation 452 into it. As shown, the walls of sample cavity 450 are curved to focus the terahertz radiation to a point in the cavity, and subsequently couple the terahertz radiation back into crystal 430 as polariton 462, whose properties can be subsequently measured. Referring to FIG. 4b, again a single non-centrosymmetric crystal 430' (e.g., lithium tantalate) forms both the excitation and detection crystals and has a trench drilled into it to form a sample cavity 450'. In this case, however, crystal 430' includes a reflective curved surface 431' at its near edge. The polariton of interest, polariton 432', propagates to the near edge and reflects from surface 431' and propagates to sample cavity 450'. Surface 431' focuses the polariton as it propagates towards the sample cavity, and the polariton couples focused terahertz radiation 452' into the sample cavity for the sample measurement.

Referring again to FIG. 1, after interaction with the sample, terahertz radiation 52 couples into detection crystal 60 as polariton 62. In the presently described embodiment, light source 20 directs temporally delayed probe beam 27 to diffract from polariton 62 and produce a signal beam 66, whose intensity is measured by a detector 70. The intensity of the signal beam corresponds to the intensity of the polariton wave at the selected time delay and selected interaction region in crystal 60. To produce probe beam 27, optical system 26 splits off a portion of the input beam from laser system 24 and sends it to an automated, optical delay line 29 (e.g., a retroreflector mounted on a mechanical translation stage) coupled to computer 80. To record the temporal response of polariton 62, computer 80 records the signal beam intensity measured by detector 70 for each of a series of temporal delays between the excitation beam 22 and probe beam 27 caused by delay line 29. In further embodiments, to enhance the diffraction measurement, the light source can also direct a temporally delayed heterodyne reference beam to interact temporally with polariton 62 and probe beam 27. The light source directs the reference beam to be collinear with the diffracted signal beam, and thus the detector measures a heterodyne signal caused by the interference of the reference and signal beams. Standard lock-in techniques can be used to further improve signal quality. Furthermore, in other embodiments, reflection of the probe beam from the polariton can be measured. In yet further embodiments, a spatially extended probe beam can be used to image polariton 62 onto a spatially resolved detector (e.g., a CCD camera) at selected time delays, with the resulting images being recorded by computer 80 for subsequent analysis. See, e.g., U.S. patent application Ser. No. 09/350, 972 filed Jul. 7, 1999 and entitled "Polariton Wave Imaging," the contents of which are incorporated herein by reference. In yet even further embodiments, the detector can include a grating and an array detector, or other suitable components, to spectrally resolve components of the signal beam to indicate spectrally selective absorption or spectral shifting caused by polariton 62. Alternatively, or in addition, the detector can be configured to measure polarization rotation in the signal beam caused by the polariton in the detection crystal. Furthermore, in other embodiments, the signal beam can be the result of nonlinear optical interaction between probe beam 27 and polariton 62 in the crystal 60, e.g., sum-frequency mixing or difference-frequency mixing, and computer 80 can derive sample properties based on the amplitude and/or phase of the nonlinearly generated signal beam.

In one embodiment, terahertz spectrometer 10 can be used as follows. A liquid sample is inserted between the generation and detection crystals 30 and 60, respectively. Alternatively, a solid sample can be inserted between the generation and detection crystals, and appropriate fluids may be used for index matching. Polariton 32 is produced in crystal 30 through ISRS with excitation beams 22 crossed at a first angle, $\theta_1$, which determines the polariton wavelength $\lambda_1$ and wavevector $q_1 = 2\pi/\lambda_1$. The polariton frequency $\omega_1$ is determined by the wavevector and the crystal dispersion relation $\omega(q)$. The polariton waves inside crystal 30 are detected through coherent scattering or imaging so that their intensity is calibrated and their timing is determined. Polariton waves corresponding to polariton 62 in crystal 60 are detected by coherent scattering or imaging, using light which is appropriately delayed to allow time for propagation. The detected signal intensity from the second crystal can be compared to that from the first to determine the amount of absorption of the terahertz-frequency radiation as it passed through the sample. The time delay and phase of the polariton signal can also be used to determine the speed of far-IR radiation in the sample and to determine the complex dielectric constant of the sample at the terahertz frequency $\omega_1$ (i.e. real and imaginary parts, which determine respectively the speed and absorption coefficient in the sample at the terahertz frequency $\omega_1$). Alternatively, or in addition, reference measurements, can be made on a reference material (e.g., a reference liquid or glass piece) positioned in the sample volume and having a known size and complex dielectric properties to provide a background calibration for the sample measurements. The process can be repeated in an automated fashion with different terahertz frequencies $\omega_1$, $\omega_2$, $\omega_3$, etc. corresponding to different crossing angles of excitation beams 22, the frequencies being spaced sufficiently close to allow for reliable interpolation of results, thereby providing complete absorption and dispersion spectra of the sample in the terahertz frequency range.

Figure 5:
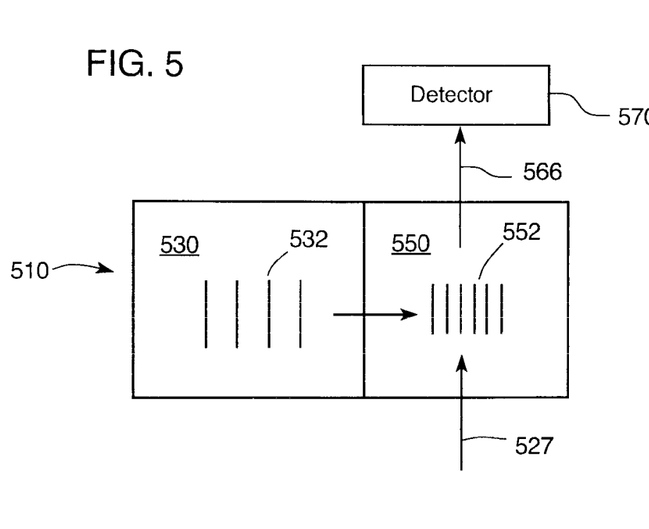
FIG. 5 is a schematic drawing of another detection arrangement for the spectrometer of FIG. 1.
Figure 6:
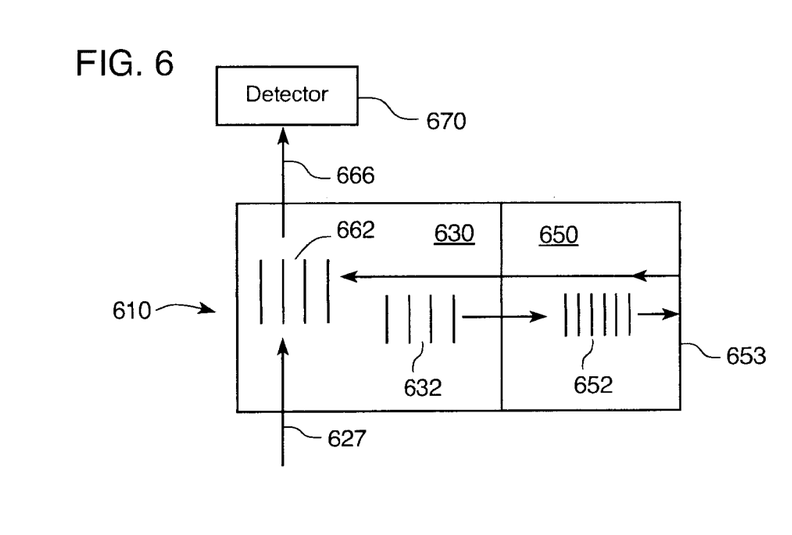
FIG. 6 is a schematic drawing of a further detection arrangement for the spectrometer of FIG. 1.

Other detection arrangements are also possible. For example, in another embodiment of a terahertz frequency spectrometer 510 shown in FIG. 5, the sample response to terahertz radiation 552 resulting from polariton 532 can be measured by interacting a probe beam 527 directly with the sample 550 itself, rather than with a detection crystal, and positioning detector 570 to measure a signal beam 566 resulting from the interaction between probe beam 527, terahertz radiation 552, and sample 550. For example, the interaction between terahertz radiation 552 and sample 550 may rotate the polarization of probe beam 527 (e.g., Kerr effect), selectively absorb part of its spectrum, shift its spectrum, diffract it, or otherwise shape it, to produce signal beam 566. The signal beam can also be produced by a nonlinear optical interaction between probe beam 527 and terahertz radiation 552 in the sample 550, e.g., sum-frequency mixing or difference-frequency mixing. Depending on which of such detection mechanisms is used, the spectrometer may include additional optics (not shown) such as polarizers, lenses, gratings, and/or wave plates. Other aspects of spectrometer 510 are the same as that described previously for spectrometer 10. In a further embodiment of a terahertz frequency spectrometer 610 shown in FIG. 6, terahertz radiation 652 resulting from polariton 632 double passes sample 650 because of a reflective interface 653 (e.g., a reflective coating) at the edge of the sample volume, and returns to crystal 630 as polariton 662. The light source (not shown) then directs probe beam 627 to interact with polariton 662 and produce signal beam 666, which is detected by detector 670. Thus, in this embodiment, crystal 630 is used for both generation and detection of the polaritons. Other aspects of spectrometer 610 are the same as that described previously for spectrometer 10.

Additional measurements can also be conducted in which a first "excitation" or "pump" event perturbs the sample, which is probed thereafter. The perturbation could be delivered by a terahertz-frequency pulse or waveform, and the probing could be conducted by a subsequent terahertz-frequency pulse or waveform. Both the excitation and probe terahertz pulses or waveforms could be launched in the excitation crystal and injected in the detection crystal as described above. The temporal delay between the excitation and subsequent probe terahertz radiation could be varied to map out the time-dependent response of the sample. Many variations of this phase-coherent pump-probe measurement are possible. For example, the first terahertz-radiation pulse could consist of many cycles of a selected frequency, i.e., be relatively narrow in bandwidth. Its effect on a heterogeneous sample could be to saturate or remove those sample components that absorbed at the selected frequency. The probe pulse could be broad in bandwidth, and it could be used to measure the absorption spectrum of the heterogeneous sample shortly after the excitation pulse. In this case a "hole" in the irradiated region of the spectrum might be observed, and the time scale for recovery of absorption in this spectral region might be measured. A variety of linear and nonlinear sample responses to terahertz radiation might be observed. Photon echo signals in the terahertz frequency range could be measured following two terahertz-frequency pulses or waveforms, with the echo signal monitored through phase-controlled heterodyne detection. In addition, visible light could be used to perturb the sample and far-IR radiation to probe its response, or far-IR radiation could be used to perturb the sample and visible light could be used to probe its response.

Also, the systems and methods described above could be used to generate and detect surface or thin film waveguide polaritons, which could be used for examination of thin samples either in contact with the surface at which the polaritons are generated or displaced laterally from that region.

The following example illustrates a measurement using one embodiment of the terahertz-frequency spectrometer.

Figure 7:
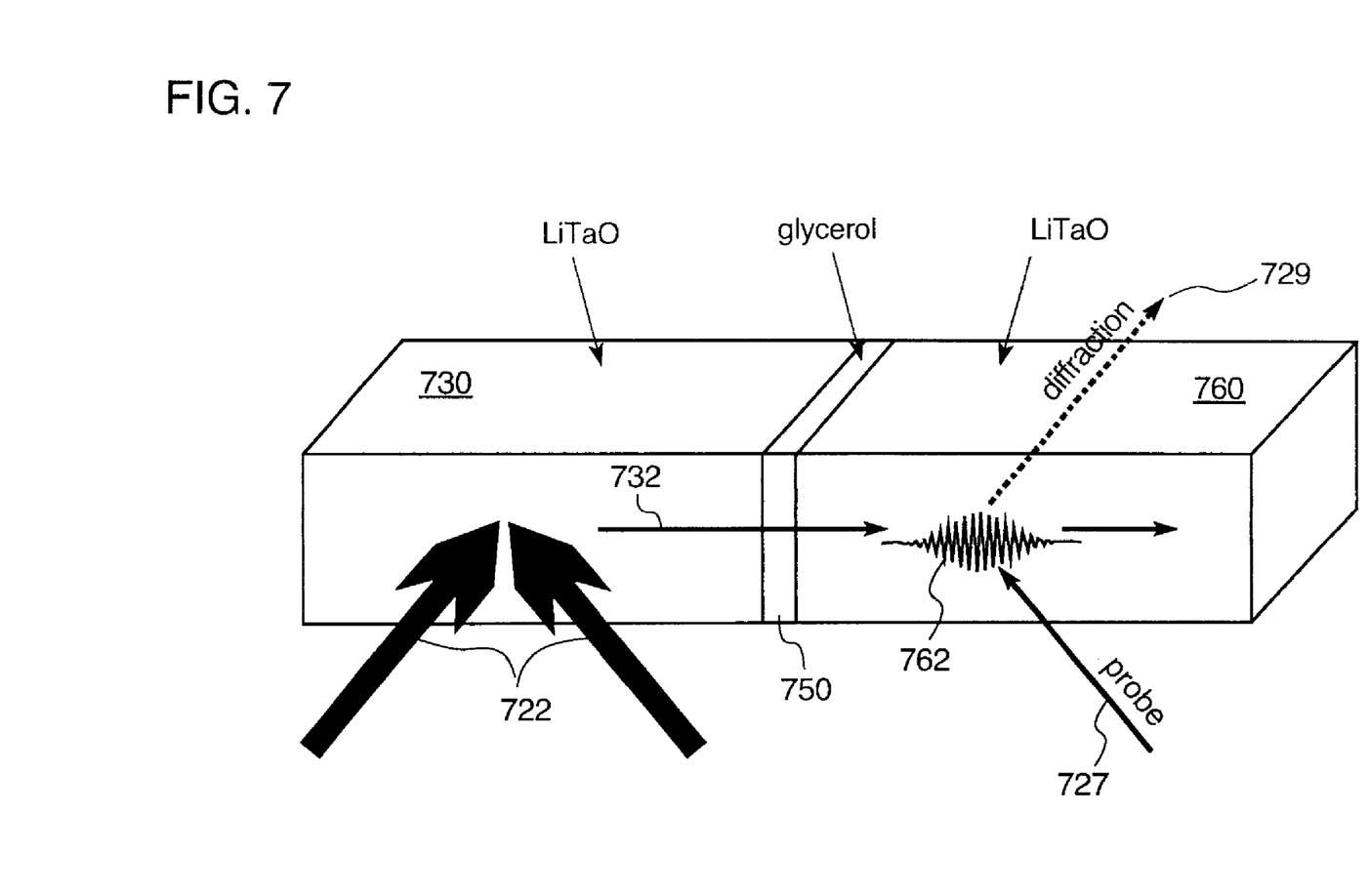
FIG. 7 is a schematic drawing of the terahertz spectrometer arrangement used in a particular Example.

Referring to FIG. 7, a sample 750 of viscous, room-temperature glycerol was sandwiched between a pair a lithium tantalate excitation and detection crystals 730 and 760, respectively. Crossed-excitation pulses 722 derived from a diffractive phase mask (consisting of parallel trenches etched into a glass substrate) and an amplified titanium sapphire femtosecond laser system operating in the visible were used to excite a phonon-polariton 732 via ISRS. The phonon-polariton response propagated through crystal 730 at the speed of far-IR radiation in the crystal (in $LiTaO_3$, about ⅙ the speed of light in air) to the crystal edge, at which its electromagnetic component couples into the sample. The terahertz radiation propagated through the sample and into crystal 760, in which it regenerates a phonon-polariton at the original frequency and wavelength. The phonon-polariton 762 in the crystal 760 was monitored through heterodyned coherent scattering of a variably delayed, visible probe pulse 727 to produce diffracted pulse 729, whose intensity was measured with a conventional silicon photodiode (not shown). The entire assembly measured roughly 1 cm in each dimension.

Figure 8:
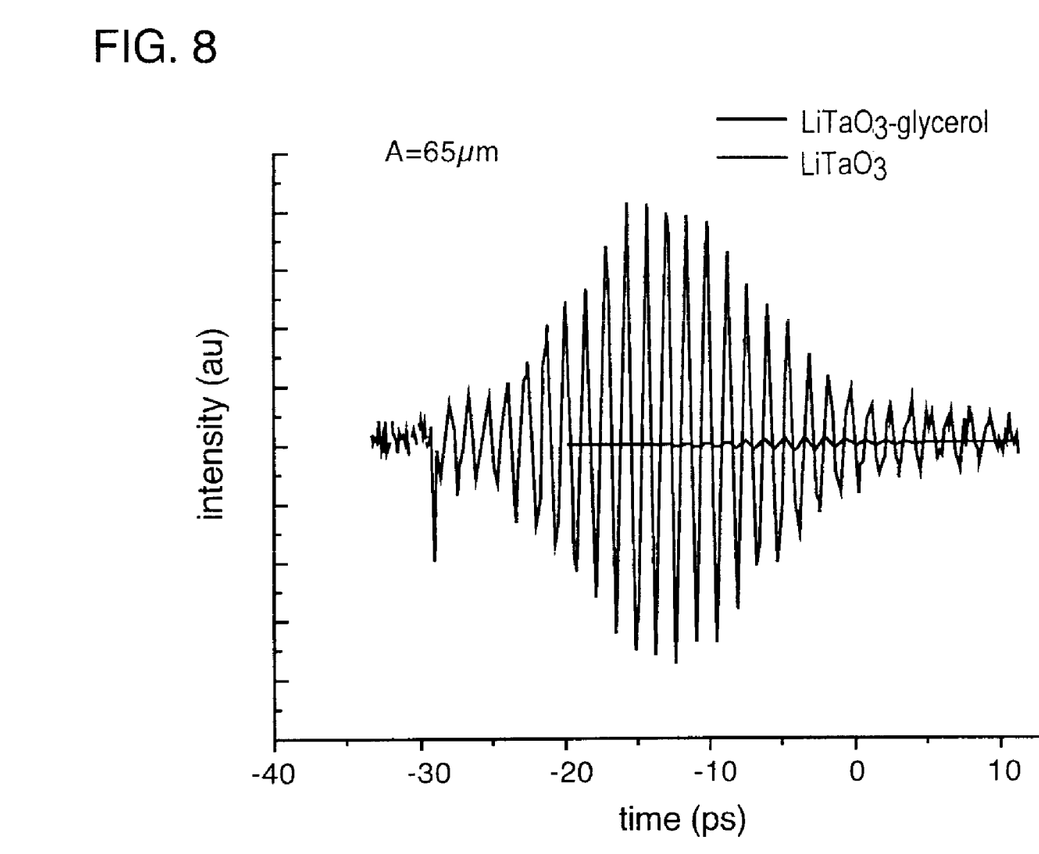
FIG. 8 is a plot of data for the Example recorded using the spectrometer arrangement of FIG. 7.

Data are plotted in FIG. 8, which plots the responses from polaritons that did and did not propagate through the liquid sample layer for comparison. The latter plot was recorded by translating the sample apparatus such that the excitation and probing beams were all within crystal 730. The attenuation and temporal shifting of the signal caused by propagation through the liquid is clearly observed from these data, revealing the complex dielectric response of the liquid at the terahertz frequencies selected.

Other aspects, advantages, and modifications are within the scope of the following claims.

What is claimed is:

1. A spectroscopic method for characterizing a sample comprising:
    positioning the sample adjacent to a non-centrosymmetric material;
    directing at least one temporal pulse of coherent EM radiation into the non-centrosymmtric material to generate a polariton therein and cause EM radiation from the polariton to propagate into the sample, wherein the polariton has a frequency less than or equal to the bandwidth of the pulse; and
    measuring a response of the sample to the EM radiation from the polariton.

2. The method of claim 1, wherein the measuring comprises:
    positioning a second non-centrosymmetric material to receive EM radiation from the sample in response to the EM radiation from the polariton in the first-mentioned non-centrosymmetric material, wherein the EM radiation from the sample propagates into the second non-centrosymmetric material to form another polariton;
    directing additional EM radiation to interact with the polariton in the second non-centrosymmetric material; and
    measuring a response of the second non-centrosymmetric material to the interaction of the additional EM radiation and the polariton in the second non-centrosymmetric material.

3. The method of claim 2, wherein the response of the second non-centrosymmetric material is measured by measuring at least one of transmission, reflection, polarization rotation, and diffraction of the additional EM radiation by the polariton in the second non-centrosymmetric material.

4. The method of claim 3, wherein the at least one of the transmission, reflection, polarization rotation, and diffraction of the additional EM radiation is spectrally resolved.

5. The method of claim 2, wherein the response of the second non-centrosymmetric material is one of sum-frequency generation and difference-frequency generation caused by the interaction of the additional EM radiation and the polariton in the second non-centrosymmetric material.

6. The method of claim 2, wherein the response of the second non-centrosymmetric material is measured by using the additional EM radiation to image the polariton in the second non-centrosymmetric material.

7. The method of claim 2, wherein the measured response of the second non-centrosymmetric material is indicative of the amplitude and phase of the polariton in the second non-centrosymmetric material.

8. The method of claim 1, wherein the measuring comprises:
    directing additional EM radiation to interact with the EM radiation in the sample from the polariton; and
    measuring a response of the sample to the interaction of the additional EM radiation and the EM radiation in the sample from the polariton.

9. The method of claim 8, wherein the second-mentioned measuring comprises measuring at least one of diffraction, reflection, a change in absorption, and a change in polarization of the additional EM radiation by the sample caused by the presence of the EM radiation in the sample from the polariton.

10. The method of claim 9, wherein the measured at least one of diffraction, reflection, the change in absorption, and the change in polarization is spectrally resolved.

11. The method of claim 8, wherein the response is one of sum-frequency generation and difference-frequency generation caused by the interaction of the additional EM radiation and the EM radiation in the sample from the polariton.

12. The method of claim 1, wherein the EM radiation from the polariton reflects from a reflecting surface and back into the non-centrosymmetric material to form a second polariton, and wherein the measuring comprises:
  directing additional EM radiation to interact with the second polariton; and
  measuring a response of the non-centrosymmetric material to the interaction of the additional EM radiation and the second polariton.

13. The method of claim 1, wherein the measured response is indicative of absorption by the sample at the frequency of the EM radiation from the polariton.

14. The method of claim 1, wherein the measured response is indicative of the refractive index of the sample at the frequency of the EM radiation from the polariton.

15. The method of claim 1, wherein the measured response is indicative of the complex refractive index of the sample at the frequency of the EM radiation from the polariton.

16. The method of claim 1, further comprising repeating the positioning, directing, and measuring for a reference sample, and comparing the measurements of the first-mentioned sample and the reference sample.

17. The method of claim 1, further comprising temporally shaping EM radiation to form the at least one temporal pulse.

18. The method of claim 1, wherein the directing comprises directing a spatially periodic pattern of the at least one temporal pulse of EM radiation onto the non-centrosymmetric material.

19. The method of claim 18, further comprising selecting the period of the spatially periodic pattern to produce a selected frequency for the polariton.

20. The method of claim 18, wherein the directing further comprises crossing at least two beams of the at least one temporal pulse of EM radiation to form the spatially periodic pattern.

21. The method of claim 18, wherein the directing further comprises passing EM radiation through a mask to produce the spatially periodic pattern on the non-centrosymmetric material.

22. The method of claim 19, further comprising repeating the selecting, directing, and measuring for multiple frequencies of the polariton.

23. The method of claim 1, further comprising focusing the EM radiation from the polariton prior to it reaching the sample.

24. The method of claim 1, wherein the sample is one of a liquid, solid, and gas.

25. The method of claim 1, wherein the sample is separated from the non-centrosymmetric material.

26. The method of claim 1, wherein the frequency of the polariton is in the range of about 0.1 to 20 THz.

27. The method of claim 26, wherein the frequency of the polariton is in the range of about 1 to 10 THz.

28. An apparatus for characterizing a sample, comprising:
  a non-centrosymmetric material;
  a sample assembly configured to support the sample adjacent to the non-centrosymmetric material;
  a light source which during operation directs at least one temporal pulse of coherent EM radiation into the non-centrosymmetric material, the at least one temporal pulse having an intensity and bandwidth sufficient to generate a polariton in the non-centrosymmetric material and cause EM radiation from the polariton to propagate into the sample, wherein the polariton has a frequency less than or equal to the bandwidth of the pulse.

29. The apparatus of claim 28 further comprising:
  a second non-centrosymmetric material positioned to receive EM radiation from the sample in response to the EM radiation from the polariton in the first-mentioned non-centrosymmetric material, wherein during operation the EM radiation from the sample propagates into the second non-centrosymmetric material to form another polariton;
  wherein during operation the light source directs a probe beam of EM radiation to interact with the polariton in the second non-centrosymmetric material; and
  a detector positioned to measure a response of the second non-centrosymmetric material to the interaction of the probe beam and the polariton in the second non-centrosymmetric material.

30. The apparatus of claim 29, further comprising a computer coupled to the light source and the detector, wherein during operation the computer analyzes the measured response to characterize the sample.

31. The apparatus of claim 28 wherein:
  during operation the light source directs a probe beam of additional EM radiation to interact with the EM radiation in the sample from the polariton, and the apparatus further comprises
  a detector positioned to measure a response of the sample to the interaction of the probe beam and the EM radiation in the sample from the polariton.

32. The apparatus of claim 31, further comprising a computer coupled to the light source and the detector, wherein during operation the computer analyzes the measured response to characterize the sample.

33. The apparatus of claim 28, wherein the sample assembly comprises a reflecting surface configured to reflect the EM radiation from the polariton back into the non-centrosymmetric material to form a second polariton, and wherein during operation the light source directs a probe beam of additional EM radiation to interact with the second polariton, and the apparatus further comprises a detector positioned to measure a response of the non-centrosymmetric material to the interaction of the additional EM radiation and the second polariton.

34. The apparatus of claim 28, wherein during operation the light source causes the at least one temporal pulse to form a periodic spatial pattern in the non-centrosymmetric material.

35. The apparatus of claim 34, wherein during operation the light source directs a pair of excitation beams to interfere in the non-centrosymmetric material to form the periodic spatial pattern, the pair of excitation beams comprising the at least one temporal pulse.

36. The apparatus of claim 34, wherein the light source comprises a laser source, a phase mask, and one or more imaging lenses, wherein during operation the laser source directs a beam to the phase mask, the phase mask diffracts the beam into multiple orders, and the one or more imaging lenses recombines the multiple orders in the non-centrosymmetric material to form the periodic spatial pattern.

37. The apparatus of claim 34, further comprising a computer coupled to the light source to control the period of the periodic spatial pattern.

* * * * *